US00PP11403P

United States Patent [19]

Doyle et al.

[11] Patent Number: Plant 11,403

[45] Date of Patent: Jun. 6, 2000

[54] MARIANNA PLUM ROOTSTOCK VARIETY NAMED 'M40'

[75] Inventors: James F. Doyle, Clovis; Robert E. Fenton, Bear Lake; Claron O. Hesse, deceased, late of Davis, all of Calif., by Eloise R. Hesse, heir

[73] Assignee: Regents of the University of California, Oakland, Calif.

[21] Appl. No.: 09/114,468

[22] Filed: Jul. 13, 1998

[51] Int. Cl.[7] ..... A01H 5/00

[52] U.S. Cl. ..... Plt./184

[58] Field of Search ..... Plt./185, 184

[56] References Cited

U.S. PATENT DOCUMENTS

P.P. 4,061 6/1977 Beakbane ..... Plt./184

*Primary Examiner*—Howard J. Locker
*Assistant Examiner*—Wendy A Baker
*Attorney, Agent, or Firm*—Burns, Doane, Swecker & Mathis, L.L.P.

[57] ABSTRACT

A new and distinct cultivar of Marianna rootstock that originated as an open-pollinated seedling is provided. The new cultivar is particularly well suited for use as prune rootstock. When compared to the previously utilized Marianna '2624' cultivar, it is found that the new cultivar exhibits superior root anchorage and a significantly reduced tendency to form unwanted suckers. Also, the new cultivar when compared per se to the Marianna '2624' cultivar is found to set considerably more fruit, to form smaller fruit, and to possess a pit that is considerably smaller. Good wet soil tolerance is exhibited. The new cultivar propagates well by the use of cuttings.

2 Drawing Sheets

BACKGROUND OF THE INVENTION

The original Marianna plum is believed to have been discovered in Texas, and is thought to be an open-pollinated hybrid of the Myrobalan plum (*Prunus cerasifera*) and the Improved Wild Goose plum (*Prunus munsoniana*). The original Marianna plum was introduced into California during the late 1800's and was used at that time as a rootstock on a relatively limited basis. In 1926, The University of California Agricultural Experiment Station selected and tested several vigorous seedlings of the Marianna plum, including what came to be known as the Marianna '2624' cultivar. Thereafter the Marianna '2624' cultivar was released into commerce in California and has become widely used a rootstock. It has been recognized; however, that the Marianna '2624' cultivar tends to form shallow roots that have a propensity to project outwards rather than downwards, and to form suckers on a prolific basis.

SUMMARY OF THE INVENTION

During late 1970, Marianna seed from various sources resulting from open-pollination was collected, was planted at the Kearney Agricultural Center of the University of California located at Parlier, Calif., and the resulting seedlings were there evaluated. The source of the seed that resulted in the production of the new cultivar of the present invention is not known; however, there is some indication that its origin may have been somewhere in Tennessee. The seeds were initially planted in the greenhouse where they germinated, and the resulting seedlings were planted in Field No. 46 during August, 1971. This research including the evaluation of the resulting test population was designated as the KHFS Project No. 57.

During 1973, each of the resulting seedlings was further evaluated and compared to the Marianna '2624' cultivar. Such evaluation has continued during subsequent years.

A single plant of the new cultivar of the present invention was discovered among the resulting seedlings which was found to possess horticultural characteristics (discussed hereafter) that were superior to those of the widely-grown Marianna '2624' cultivar. Had the new cultivar of the present invention not been discovered and preserved it would have been lost to mankind.

The new Marianna plum cultivar of the present invention was found to exhibit:

(a) superior rooting anchorage when compared to the Marianna '2624' cultivar (non-patented in the United States), (b) a substantially lesser propensity to form suckers than the Marianna '2624' cultivar; and (c) the ability to well serve as a prune rootstock.

The roots of the new cultivar were found to extend more deeply and more vertically into the ground, while those of the Marianna '2624' cultivar tend to project outwards at a substantially shallower depth. More specifically, the new cultivar generally forms more deeper roots and forms more roots that exceed a 20 degree angle from the horizontal ground surface than the Marianna '2624' cultivar. Specific root depths vary with the soil conditions that are encountered at a given growing location. The substantially lesser sucker formation offers a significant savings in labor.

It also has been found that when compared to the Marianna '2624' cultivar per se, the new cultivar of the present invention forms considerably more fruit, forms smaller fruit, and forms a considerably smaller pit. Since the fruit developed on this rootstock cultivar is of no economic value, these comparisons are made simply for identification purposes. The Marianna '2624' cultivar is believed to be a triploid and produces very few fruit. The new cultivar of the present invention is most probably a standard diploid and produces a moderate crop of small cherry-sized fruit. The quantity of fruit produced on the new cultivar can vary substantially from year to year, but is always more than that produced by the Marianna '2624' cultivar.

The new cultivar of the present invention has served well as a French prune and Santa Rosa plum (*Prunus salicina*) rootstock. No need for interstem usage has been experienced. When used as a rootstock a varietal top (i.e., scion) is budded to the new cultivar. When compared to the Marianna '2624' cultivar, no differences in tree size, fruit size, precocity, etc. have been observed in the scion tree grown on such rootstocks. While not evaluated to date, the new cultivar may also offer potential for service as a rootstock for Japanese plum, and apricot. Peach (*Prunus persica*) has been observed to be incompatible with the new cultivar of the present invention.

Beginning in late fall of 1973 the new cultivar of the present invention has been reproduced at Parlier, Calif. by cuttings after pretreatment with a rooting hormone. Such propagation has confirmed that the characteristics of the new cultivar are stable and are reliably transmitted to subsequent generations.

The new cultivar of the present invention has been named 'M 40'.

BRIEF DESCRIPTION OF THE PHOTOGRAPHS

The accompanying photographs show specimens of fruit and plant material of the new cultivar as depicted in color as nearly true as it is possible to make the same in a color illustration of this character. The tree of the new cultivar was grown at the Kearney Agricultural Center of the University of California located at Parlier, Calif.

DETAILED DESCRIPTION

Figure 1:
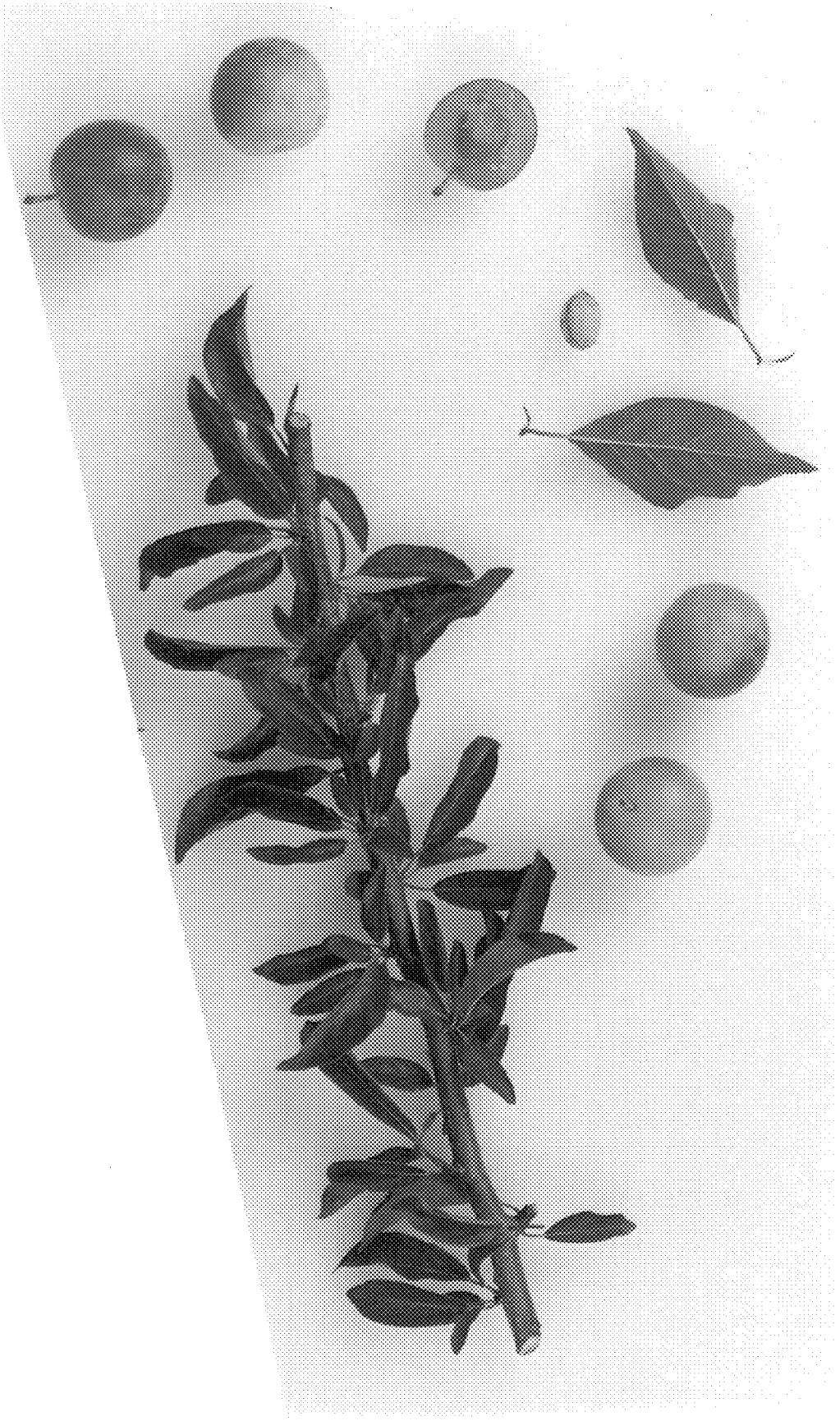
FIG. 1 illustrates mature wood with foliage, fruit, fruit flesh, stones, and under leaf surfaces.
Figure 2:
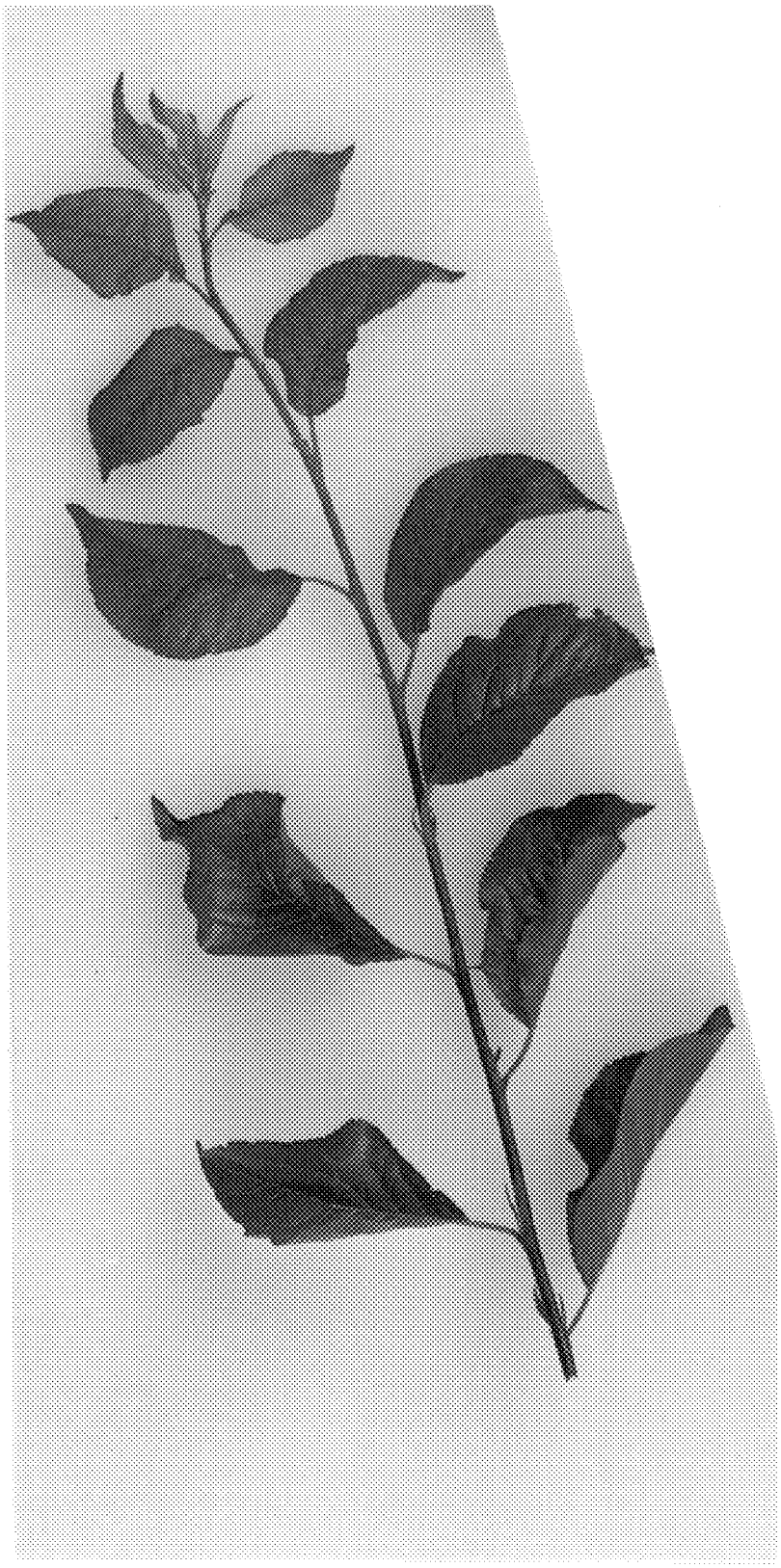
FIG. 2 illustrates a specimen of a young shoot.

The folllowing is a detailed description of the new cultivar obtained during the 1996 growing season. The tree was grown at the Kearney Agricultural Center of the University of California located at Parlier, Calif. The tree had been planted during the spring of 1987 as a self-rooted cutting. Color designations are presented with reference to the "Dictionary of Color" by Maerz and Paul, First Edition (1930).

Botanical classification: Marianna plum (*Prunus cerasifera×Prunus munsoniana*), cv. 'M 40'.

Tree:

*Size.*—The tree entering its eleventh year had a height of approximately 5.49 to 6.1 meters, and a breadth of approximately 7.32 to 7.92 meters across the crown.

*Vigor.*—Vigorous.

*Growth.*—Upright to upright-spreading in form and generally trained in an open vase system with six primary scaffolds.

*Hardiness.*—Hardy under typical San Joaquin Valley climatic conditions.

*Production.*—Moderately productive.

*Bearing.*—Regular bearer.

Trunk:

*Size.*—Relatively thick. The trunk diameter of the original tree at 10 cm. above the ground is approximately 23 to 24 cm.

*Texture.*—Relatively rough with medium amounts of scarfskin.

*Color.*—The bark color ranges from grey (15-A-1) to grey-brown (15-A-6 Beaver Brown).

*Lenticels.*—Large in size and moderate in number. Often the lenticels are strung together horizontally in rows with an overall length of approximately 2 to 6 cm. Typically the lenticels range from approximately 4 to 14 mm. in length and approximately 1.5 to 2.5 mm. in height.

Branches:

*Size.*—Medium, and slightly smaller than that of the Marianna '2624' cultivar.

*Texture.*—Smooth on current season's growth and becomes slightly ridged with moderate scarfskin as maturity advances.

*Color.*—Mature shoots are grey-brown (15-A-6 Beaver Brown) to green-brown (15-J-5 Olive Drab). The current season's shoots are light green (20-L-5 Lettuce Green) with some reddish overtones on surfaces exposed to sunlight. With maturity the shoots become somewhat purplish (7-H-5 Aubusson). The color of the expanding shoot tip commonly is light green-yellow (18-K-2).

*Internode length.*—Variable on small shoots and within the normal range. The length between nodes commonly is approximately 17 to 32 mm.

*Crotch angle.*—Noticeably wider than that of the Marianna '2624' cultivar. For instance, crotch angles commonly are 15 to 30 degrees flatter than those of the Marianna '2624' cultivar.

Leaves:

*Size.*—Small to medium in size for a Marianna plum. Typical length from vigorous current season's growth is approximately 7.4 to 9.1 cm. including the leaf petiole, and typical width is approximately 4 to 4.8 cm. The leaf thickness is average. Those leaves that are present on spurs tend to be substantially smaller and tend to be irregular in configuration, often having only approximately one-half the length as other leaves borne on shoots and usually are more elongated.

*Form.*—Variable from oval to slightly obovate.

*Apex.*—Acute and often is slightly twisted sideways.

*Color.*—The upper surface is dark green (23-L-4 Quaker Green) to even darker green (24-L-6). The lower leaf surface is lighter green (22-K-4 to 22-L-8). The lower veins, especially the midvein, are a pale yellow-green (17-J-6).

*Margin.*—Serrate apically and along the mid-margins and approximately crenate along the basal margins. The serrations are large and somewhat irregular. The leaf margins are moderately undulate.

*Petiole.*—Generally medium in size, commonly approximately 11 to 15 mm. in length, approximately 1 to 1.5 mm. in thickness, pale green (19-J-5) when young, and often becoming tinged red-purple (7-J-8 Domingo Red) with advancing maturity. The reddish coloration is less apparent within the petiole groove. The upper surface is quite pubescent and of medium length and with fine pubescence on the upper petiole surface along the top of the petiole groove ridges. The petiole is relatively glabrous on under surface.

*Glands.*—Very small in size. Commonly no glands are present on the petiole. One or two glands are present at times at the base of the leaf margin and are often on short stalks. The glands usually are globose in form and alternate in position. The coloration is variable from green (21-K-7) to reddish (4-I-10).

*Stipules.*—Linear lanceolate in configuration, semi-persistent, margins are serrate, commonly approximately 7 to 11 mm. in length, and the coloration of the stipules is green (20-J-7) to 20-J-9).

Fruit:

*Maturity when described.*—Full ripe condition with moderate give to the fruit when squeezed and with a juicy interior.

*Picking.*—The fruit ripened from Jun. 7 to 14, 1996.

*Size.*—Small and relatively uniform. Average axial diameter is approximately 26 to 32 mm., the average suture diameter is approximately 26 to 32 mm., and the average cheek diameter is approximately 26 to 34 mm. The fruit is of such small size that it has no significant commercial value as a fresh fruit.

*Form.*—Variable in form, globose to oval in lateral aspect, and in the apical aspect varies from globose to slightly oval. The fruit commonly is quite symmetrical.

*Suture.*—Thin and consists of an inconspicuous line extending from the base to the apex of the fruit. The suture is smooth or only slightly depressed. No stitching or callousing commonly is present on the suture surface. The suture line is variable in coloration, and often but not always matches the color of the surrounding area. The suture coloration varies from red (2-H-11 Tangerine) to yellow (10-J-2 Citron Yellow).

*Ventral surface.*—Quite smooth and regular.

*Base.*—Variable from rounded to slightly truncate. The base angle commonly is slightly oblique to the fruit axis.

*Stem cavity.*—Very small and slightly depressed, approximately 4 to 6 mm. in length, approximately 4 to 6 mm. in width, and approximately 1 to 2 mm. in depth. No special coloration or markings have been observed within the cavity basin.

*Apex.*—Commonly rounded and smooth.

*Pistil point.*—The pistil point is apical and is in the form of a small callous scar of approximately 1 to 1.5 mm. in diameter. At times the callous area of the apex is somewhat sunken.

*Stem length.*—Commonly approximately 6 to 10 mm.

*Stem thickness.*—Commonly approximately 1 to 2 mm.

*Stem color.*—Variable from light green (18-J-3) to pale greenish-yellow (18-I-1) and at times with brownish-green areas (13-K-6).

*Skin pubescence.*—Is glabrous.

*Skin flavor.*—Highly acid.

*Skin tenacity.*—Very tightly attached to the flesh at maturity.

*Skin thickness.*—Variable.

*Skin tendency to split.*—None observed.

*Skin color.*—Variable with a red blush and a yellow ground color (10-K-4 Narcissus). The red blush can vary from approximately 25 to 100 percent of the skin surface. The red commonly is present in a washed pattern which varies in intensity from bright red (3-K-11 Flash Red) to orange-red (2-G-11). At times numerous very small calloused lenticel dots are visible especially over the red blushed areas. The yellow ground color commonly is present on most of the fruit and often varies from approximately 10 to 75 percent of the fruit surface. The fruit surface tends to be covered with a light greyish bloom.

*Flesh color.*—Somewhat variable. In general is yellow amber (9-K-4 Jasmine). Many fruits exhibit this flesh coloration from skin to stone. As the fruit matures, some red coloration can appear in the flesh (2-J-11 Brigand Red), as well as in fibers adjacent the stone.

*Flesh texture.*—Moderately firm, and when ripe is juicy and slightly fibrous.

*Ripening.*—Ripens evenly throughout.

*Flavor.*—Moderately acidic; however, the skin and flesh next to the stone are highly acidic.

*Aroma.*—Mild and somewhat vinous.

*Eating quality.*—Relatively poor, generally acidic and not recommended for consumption.

*Stone type.*—Full clingstone with numerous fibers connected to the flesh over the entire surface of the stone.

*Stone size.*—Small and commonly ranges from approximately 15 to 18 mm. in length, approximately 11 to 13 mm. in width, and approximately 7 to 8 mm. in thickness. The stone is approximately one-half the size as that of the Marianna '2624' cultivar.

*Stone form.*—Somewhat variable, most frequently oval, and at times approaching ovate.

*Stone base.*—Tapered, very slightly truncate, and the base angle is variable from slightly to fully oblique at a right angle to the stone axis.

*Stone hilum.*—Very small and generally oval in form.

*Stone apex.*—Low and very weakly acute.

*Stone sides.*—Commonly vary from equal to very slightly unequal.

*Stone surface.*—Lateral stone surfaces are relatively smooth, only very slightly roughened and with only an occasional low ridge, and at times the ventral edge is subtended by two substantial grooves.

*Ventral edge.*—Moderately wide, only slightly protruding, and most prominent basally.

*Dorsal edge.*—A wide but shallow groove is present along the dorsal edge from the base to near the mid-point of the suture where it abruptly terminates. The apical shoulder of the dorsal suture is relatively smooth and is substantially uniformly rounded.

*Stone color.*—When dry, light tan-brown (12-I-7 Desert) to a slightly darker tone (12-K-8 Spruce Yellow). Occasionally more mature stones have areas of slight red staining.

*Fibers.*—Short, light colored, and present on the stone surface.

*Tendency to split.*—None observed.

Flowers:

*Chilling season.*—Very low for the growing location. There were approximately 609 chilling hours below 45° F. for the 1995–1996 winter season. This was one of the lowest chilling winters on record.

*Buds.*—Small in size, conic in form, plump, slightly appressed to the bearing site, and approximately 1.5 to 2 mm. in length. The exterior bud is light chestnut brown (7-H-12 Mohawk Brown) in coloration. The surface of the bud scales is glabrous. The buds are hardy under typical climatic conditions of the San Joaquin Valley. There commonly are two to four floral buds per node and most frequently two floral buds per node.

*Bloom timing.*—First bloom on Mar. 5, 1996. Full bloom on Mar. 13, 1996. The date of bloom was substantially the same as that of the Marianna '2624' cultivar. The duration of the bloom period on the entire tree commonly is approximately 14 days.

*Size.*—The flower size is small to medium. The fully expanded flower diameter commonly is approximately 12 to 17 mm.

*Bloom quality.*—Abundant.

*Petals.*—The petal size is small to medium and commonly ranges from approximately 7 to 10 mm. in length and from approximately 7 to 8 mm. in width. The petal number is five. The petal form is broadly ovate. The petal color is white (1-A-1). The petal claw is short, approximately 0.5 to 1 mm. in length, and truncate in form. The petal margins are undulate and highly ruffled when young. Most petals are substantially cupped upwards and inwards even at full maturity. The petal apex is generally rounded, slightly domed, and often is cupped inwards.

*Pedicel.*—Short and commonly exhibits a length of approximately 3 to 5 mm. and a thickness of approximately 0.75 to 1 mm. The coloration is light green (18-I-6) and the surface is glabrous.

*Nectaries.*—Light amber-orange (12-L-6) when young becoming slightly darker at maturity.

*Calyx.*—Glabrous and slightly ridged and the coloration is light brown-green (13-L-3). The ribbed areas are lighter green (20-J-3 Shadow Green).

*Sepals.*—Small and narrowly conic in form and green (20-K-5 Verdant Green) in coloration. Most of the exterior surface is glabrous, but the margins tend to be pubescent with relatively long white pubescence. The margins are serrate at times and often edged with white and occasionally tinged with red or rose coloration.

*Anthers.*—Small in size, and bright yellow-orange (9-L-4 Sunflower) in coloration.

*Stamens.*—Variable in length and commonly range from approximately 4 to 7 mm. in length. Almost always extend above the pistil. The coloration is white (1-A-1).

*Pollen.*—Abundant yellow-orange (9-L-4 Sunflower).

*Pistil.*—Glabrous. The length commonly is approximately 5 to 6 mm. including the ovary. The coloration basally is pale green (18-J-2).

Major use: Rootstock for prunes.

Resistance to insects and diseases: Believed to be comparable to the Marianna '2624' cultivar.

Wet soil tolerance: Good. Resistance to the rootknot nematode has been observed.

*Pollination requirement.*—Not determined since the fruit is of inferior size and quality and has no commercial significance.

We claim:

1. A new and distinct cultivar of Marianna plum which exhibits the following combination of characteristics:

(a) superior rooting anchorage when compared to the Marianna '2624' cultivar (non-patented in the United States), (b) a substantially lesser propensity to form suckers than the Marianna '2624' cultivar, and (c) the ability to well serve as a prune rootstock;

substantially as illustrated and described.

* * * * *